United States Patent [19]
Boyd

[11] Patent Number: 5,732,415
[45] Date of Patent: Mar. 31, 1998

[54] ADJUSTABLE PET EYEWEAR

[76] Inventor: David J. Boyd, 11500 SE. Mather Rd., Clackamas, Oreg. 97015-8258

[21] Appl. No.: 804,935

[22] Filed: Feb. 24, 1997

[51] Int. Cl.⁶ .................................................. A61F 9/02
[52] U.S. Cl. .................... 2/426; 2/445; 2/452; 119/836; 54/802; 351/41; 351/157
[58] Field of Search ........................ 2/426, 15, 445, 2/452; 119/850, 836; 54/80.2; 351/41, 90, 157

[56] References Cited

U.S. PATENT DOCUMENTS

| | | | |
|---|---|---|---|
| 888,687 | 5/1908 | Boggs | 119/850 |
| 903,108 | 11/1908 | Rogers | 119/850 |
| 2,190,115 | 2/1940 | Fuqua | |
| 2,407,029 | 9/1946 | Miller | |
| 3,924,388 | 12/1975 | Morrison | |
| 4,178,742 | 12/1979 | Longfellow | |
| 4,756,145 | 7/1988 | Pelling | |
| 5,093,940 | 3/1992 | Nishiyama | |
| 5,148,354 | 9/1992 | Alfaro et al. | |
| 5,406,340 | 4/1995 | Hoff | 2/452 |

*Primary Examiner*—Gloria M. Hale
*Attorney, Agent, or Firm*—Marger, Johnson, McCollom & Stolowitz, P.C.

[57] ABSTRACT

The present invention is an eye protection device adapted to be worn by a canine. The device comprises an eye enclosure element such as a transparent plastic goggle which is adapted to rest snugly against the face of a canine. A pair of side straps extend from opposing sides of the eye enclosure element to connect to a collar adapted to be worn about the neck of the canine. The side straps are length adjustable as by hook and loop attachments, snaps or pawl mechanism and couple to the collar along a selected length of the collar thereby allowing two-dimensional adjustment of the side straps. A preferred embodiment of the invention further includes a pivot element for easily rotating the eye enclosure element away from the eyes of the canine when the invention is not needed. Alternately, the invention can include anti-lift and anti-loss straps for maintaining use of the invention when the wearing animal is using the invention in inclement conditions.

20 Claims, 3 Drawing Sheets

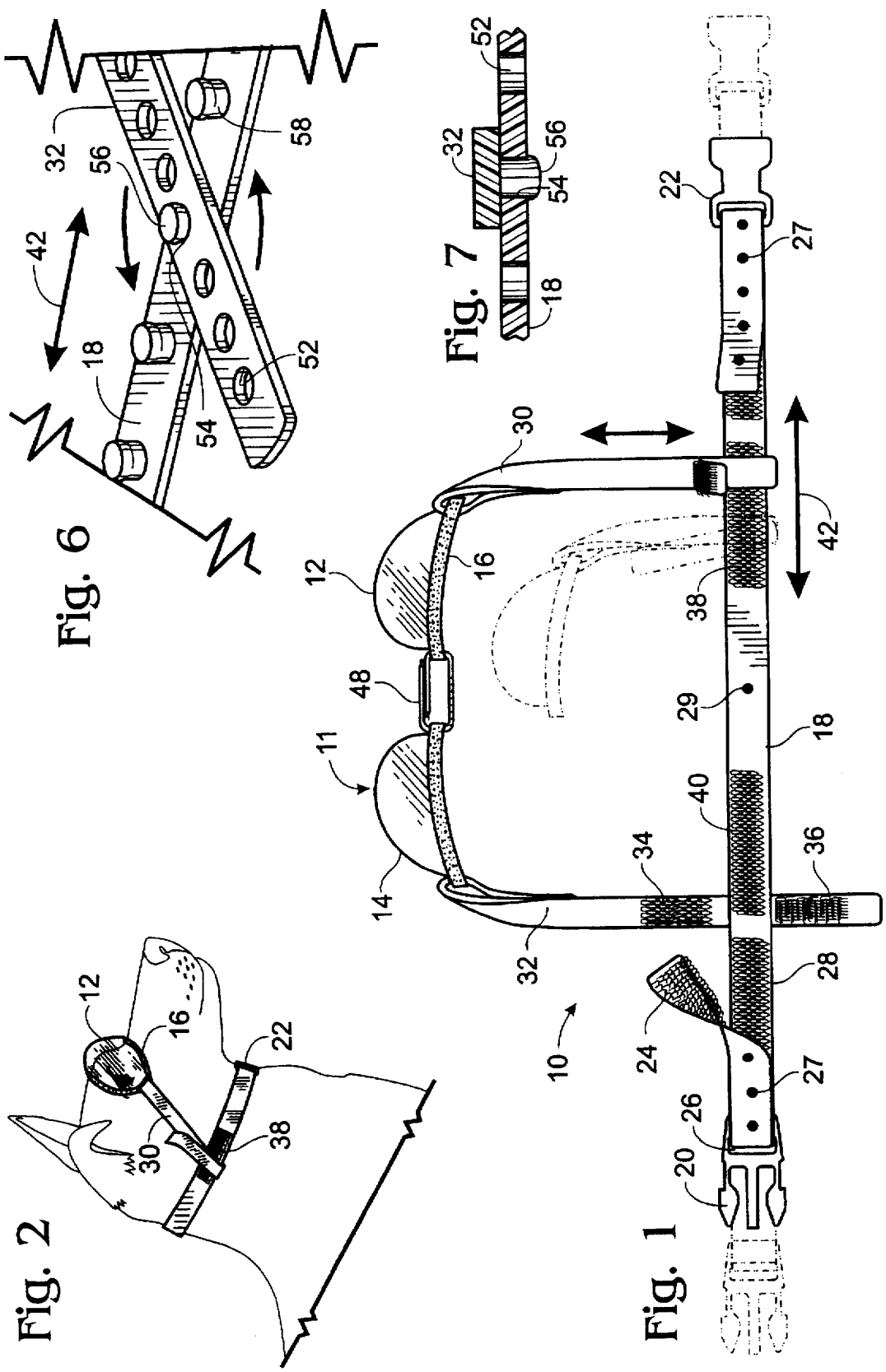

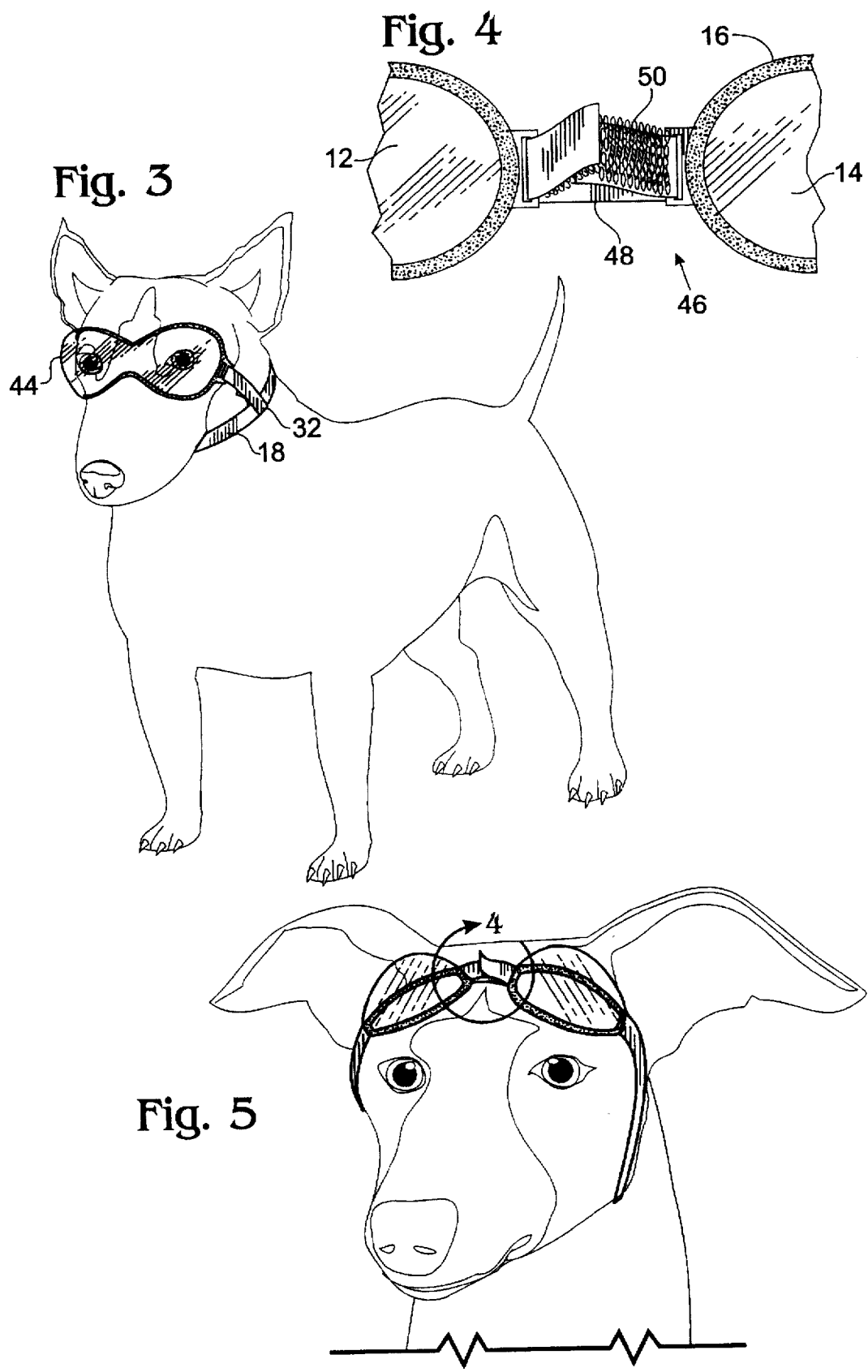

ADJUSTABLE PET EYEWEAR

BACKGROUND OF THE INVENTION

This invention relates generally to eye protection devices, and more particularly, to an eye protection device especially adapted for use by dogs or other such pets.

Eyewear in humans has served a variety of purposes—from fashion to vision correction to eye protection. The most common type of eyewear is the conventional set of eyeglasses which include a set of curved glass or plastic lenses that are positioned in front of the eyes to correct for vision problems such as myopia. These lenses are set within a frame that is supported by the bridge of the nose of the human wearer and are maintained in position by curved extensions which extend partially around the back of the ear. Eyeglasses, however, have been known to fall off. Thus, for more active persons, a strap is connected to the curved extensions of the frame and placed snugly about the back of one's head.

Problems arise when fitting eyewear to animals where the physiology of the crania is very different from that of humans. In most mammalian vertebrated animals, the mandible and muzzle extend far beyond the anterior surface of the cranium. Therefore, it is far more difficult to adapt securing means that will maintain an eyewear device in position on the cranium of the animal. Another difference between the human head and an animal head is that the anterior surface of the cranium of a human is relatively vertical as compared to the angled anterior surface of the cranium for an animal. Because of this difference, any animal eyewear device must be contoured so as to account for this angled cranial shape.

Early known animal eyewear devices were adapted for use by horses. For example, U.S. Pat. No. 2,407,029 discloses an eye shield design for use by equines comprising essentially a hood having eyehole blinders which is secured to the head of a horse by straps tied underneath the chin or neck of the animal.

The need for protective eyewear also exists for use with pets, and primarily dogs, who enjoy hanging their heads out of the windows of moving cars. Perhaps this is because they enjoy the feel of the wind against their skin. Perhaps it is simply that they like to look outward at the passing countryside. The world may never know. Nevertheless, such behavior is detrimental to dog's eyes which tend to dry out or get dust and other objects in them in the typical moving car scenario described above.

There have been a few devices known in the art which are adapted for use by dogs and the like. U.S. Pat. No. 3,924,388 to Morrison discloses an eye protective device for animals comprising a flexible mask to be worn over the face of a dog and having a cutout over which a plastic shield is placed. The eye protective portion of the device is attached to the dog's head via a chin strap and back of the head via a head strap. A similar device is disclosed in U.S. Pat. No. 4,178,742 to Longfellow. Longfellow discloses protective animal goggles which consist of a onepiece goggle window conformed to a dog's head via a flexible envelope. Elastic straps connected to the envelope are adapted to encircle the dog's head and chin.

A recognized difficulty with designing head or eyewear for dogs is the variety of breeds, giving extremes in both size and shape of the crania and neck region. For instance, some breeds might have closer set eyes while another breed might have a longer nose. Both the Morrison and Longfellow devices are cumbersome for the dog to wear thus increasing the discomfort level. More importantly, however, neither of the above devices has simple manual adjustment means which will allow the eyewear to easily and comfortably adapt to the head shape of a variety of different breeds of dogs.

Accordingly, a need remains for adjustable pet eyewear which solves the drawbacks of these prior art devices.

SUMMARY OF THE INVENTION

It is, therefore, an object of the invention to protect the eyes of animals, and particularly canines.

It is another object of the invention to provide a protection device which is adaptable for use by animals having differently sized and shaped cranial features.

The present invention is an eye protection device adapted to be worn by a canine, comprising: eye enclosure means having a substantially transparent forward element and a peripheral edge which is adapted to rest snugly against the face of a canine; a neck encircling collar adapted to be worn about the neck of the canine; left and right side straps coupled on opposing sides of the eye enclosure means and connecting said means to said neck encircling collar; and left and right side strap length adjustment and lateral attachment means adapted to couple said left and right side straps along a selected length of said collar. The side strap length and lateral adjustment means are preferably formed of complimentary hook and loop portions which can be mated together along an elongate length of the portions to allow two-dimensional adjustments. A preferred embodiment of the invention further includes pivot means for easily moving the eye enclosure means to the top of the head and away from the eyes of the canine when the invention is not needed. Alternately, the invention can include anti-lift and anti-loss means for maintaining use of the invention when the wearing animal is using the invention in inclement conditions.

The foregoing and other objects, features and advantages of the invention will become more readily apparent from the following detailed description of a preferred embodiment of the invention which proceeds with reference to the accompanying drawings.

BRIEF DESCRIPTION OF THE DRAWINGS

FIG. 1 is a top plan view of a preferred embodiment of the eye protection device constructed according to the present invention.

FIG. 2 is a side elevation view of the device of FIG. 1 as worn by a dog.

FIG. 3 is a perspective view of another embodiment of the invention as worn by a dog.

FIG. 4 is a detailed front view of the device of FIG. 1 showing the lens width adjustment means.

FIG. 5 is a perspective view showing the eye protection devices of FIG. 1 in a raised position on a dog.

FIG. 6 is a perspective view showing a second embodiments of the side strap length adjustment and lateral attachment means.

FIG. 7 is a sectional view showing a third embodiment of the side strap length adjustment and lateral attachment means.

DETAILED DESCRIPTION

Figure 8:
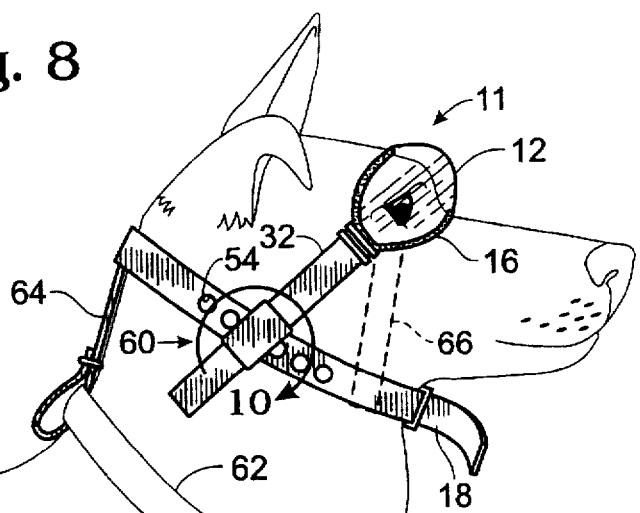
FIG. 8 is a side elevation view showing another alternate embodiment of the invention.

FIG. 1 shows a preferred embodiment of an eye protection device 10 constructed according to the present invention which is adapted to be 5 worn by a canine or similar animal. Device 10 includes eye enclosure means having a substantially transparent forward element, here shown by clear plastic lenses 12 and 14. Lenses 12,14 can be formed using molded, shatter-resistant eye-lenses that are bubble shaped for comfort and have a wide angle of view. Exemplary types of lenses which can be used are clear lenses, tinted lenses, light adjusted lenses, vision correction lenses, post operative lenses and fluorescent or night vision lenses. The eye enclosure means preferably include a deformable peripheral edge 16 which is adapted to rest snugly against the face of a canine when device 10 is worn. For example, peripheral edge 16 can be made of a spongy synthetic resin such as urethane or neoprene rubber.

Device 10 also includes an elongate neck encircling strap or collar 18 adapted to be worn about the neck of the canine, as by placing the open collar about the area between the neck and chin of the dog and fitting the bayonet clip 20 into the receiving buckle 22. Strap 18 includes means for adjusting the length of the collar to fit a variety of dog neck sizes. In the preferred embodiment shown, the length adjustment means includes complimentary hook and loop portions, such as those marketed under the Velcro® name, positioned at the terminal ends of strap 18. For example, as shown in FIG. 1, hook portion 24 is received through a slot 26 in clip 20 and folded back against a selected length of complimentary loop portion 28. Buckle 22 can also include a complimentary set of hook and loop portions to allow lengthening of the neck encircling strap 18, as between the two positions shown by solid lines and dot-dashed lines.

Strap 18 can include reference indicators spaced along its ends, such as dot 27, to facilitate adjustment of the strap to a desired length. Strap 18 can further include a centering indicator, such as dot 29. Dot 29 can be centered adjacent the backside of the dog's head or neck for a proper fitting of the eye protection device 10.

Device 10 further includes left and right side straps 30,32 coupled to opposing sides of the eye enclosure means 11 and connecting said means to the neck encircling collar 18. Since it is anticipated that the distance between the worn neck-encircling strap and the eye enclosure means will be different for different breeds of canines, it is preferable that the side straps 30,32 include length adjustment means. This can include various means such as a buckle, a pawl mechanism, Velcro® (FIGS. 1 and 2), eyelet snaps (FIGS. 6 and 7), and the novel pivot means shown in FIGS. 8–10. Straps 18, 30 and 32 can be made of any suitable material such as an elastic or plastic webbing material, leather or the like.

FIGS. 1 and 2 shows the preferred embodiment of the length adjustment means formed of complementary hook and loop portions, such as Velcro® hook portion 34 and loop portion 36, mounted on a same side of each of the left and right straps 30,32. As shown in FIG. 1, the hook portion 36 on left side strap 32 is adapted to fold over the neck-encircling strap 18 and against the complimentary loop portion 34. FIG. 1 shows a dot-dashed outline of the right side strap 30 adjusted for length on a smaller dog as by folding over a greater length of hook portion 36.

A further feature of device 10 is lateral adjustment means enabled by an elongate hook or loop portion, such as loop portion 40, mounted along a length of the collar 18 which is complimentary to a portion 36 mounted on the side strap 32. This can be seen in FIG. 1 which includes elongate Velcro® portions 38,40 affixed along a particular length 42 of collar 18. The side straps 30,32 are positioned along length 42 and folded over so that one element of the Velcro® material, such as Velcro® hook portion 36, couples with the complimentary material, such as elongate Velcro® loop portion 40, on the collar 18.

FIG. 3 shows an alternate embodiment of the eye enclosure means 11, including a one-piece, transparent forward element 44 in a first or lowered position around the eyes of the canine. The preferred eye enclosure means, however, is a two piece unit as shown in FIG. 4 which includes lens width adjustment means 46 comprising a flexible strap 48 coupled between lens units 12 and 14 and having complimentary Velcro® attachment means 50. This embodiment allows greater flexibility in fitting all shapes and sizes of canines with the goggles wherein not only are the width of the lens units adjustable, but also their rotated position with respect to each other. Thus, for instance, pug nosed dogs will be fitted just as easily as long-nosed dogs, such as the one shown in the figures. Additionally, the eye enclosure means can be moved upward to a second or raised position as shown in FIG. 5, as by the pivot means described below, and away from the eyes of the dog so that they rest on the top of the dog's head either in front of or behind the dog's ears.

FIGS. 6 and 7 show alternate embodiments of the side strap length adjustment and lateral attachment means. FIG. 6 shows a perspective view of side strap 32 having a plurality of apertures, such as eyelets 52, 54, disposed along its length. A plurality of projections, such as snaps 56,58, are disposed along length 42 of collar 18 and are adapted to be received within one of the eyelets. To adjust the effective length of side strap 32, one of the plurality of eyelets, such as eyelet 52 or 54, would be positioned over and pressed onto a snap, such as snap 56. To adjust the lateral placement of side strap 32 along length 42 of collar 18, one would position one of the snaps, such as snap 56 or 58, within a selected eyelet 54.

FIG. 7 illustrates a cross-section of an alternate embodiment of the side strap length adjustment and lateral attachment means where the snaps 56 are located on the side strap 32 and the eyelets 52,54 are located on the collar 18. As can be seen, snap 56 has a slightly deformable rounded head portion which is of a slightly larger diameter than eyelet 54 so that, once pressed within eyelet 54, snap 56 is secured. For example, these snaps and eyelets could be similar to those worn on the back of a baseball cap to facilitate adjustment thereof.

FIG. 8 shows yet another alternate embodiment of the invention. Shown are lens element 12 and peripheral edge 16 coupled to side strap 32 which in turn is coupled to neck-encircling collar 18 by pivot means 60 discussed in more detail below. The dog illustrated in FIG. 8 has a conventional dog collar 62 which typically hangs relatively loosely around the lower portion of the neck. In order to further maintain the eyewear device on the head of the wearing animal, anti-loss means, shown by antiloss strap 64, is coupled between the neck-encircling collar 18 and the dog collar 62.

An alternate feature, shown in dashed lines, comprises an anti-lift means for preventing the eye enclosure means from moving from its desired position around the animal's eyes. As will be appreciated by the description below, the anti-lift means ensures that the lenses will not lift up when the dog is unattended, such as when hunting in heavy brush. The anti-lift means according to a preferred embodiment of the invention comprises a second right side straps 66 connected at one end to one side of the eye enclosure means 11 (here, the right lens element 12) and connected at another end to collar 18 in spaced apart relation to the first right side strap 32. It is understood that the anti-lift means includes a second left strap (not shown) which is similarly positioned on the left side of the device and can be attached to collar 18 via snap, hook and loop, buckle or hook-end.

Figure 9:
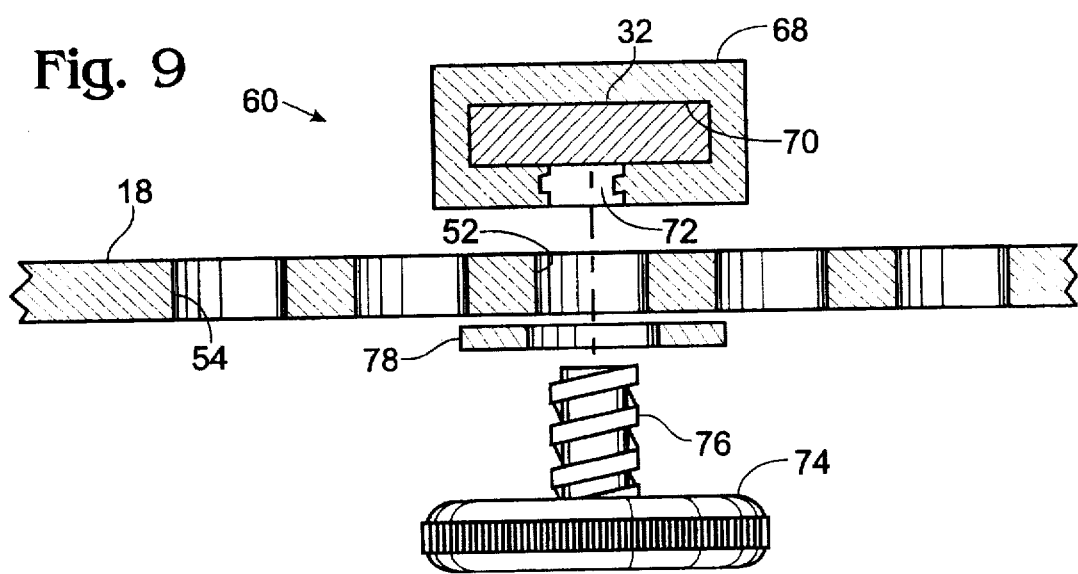
FIG. 9 shows the pivot means feature of the device of FIG. 8 in exploded sectional view as taken along line 9—9 in FIG. 10.

FIG. 9 shows a sectional exploded view of the pivot means 60 constructed according to a preferred embodiment of the invention. The pivot means facilitates movement of the eye enclosure means 11 to a raised or lowered position on the animal while maintaining tension on the side straps to which it attaches. The pivot means includes an eyelet along the length of the collar, such as shown by eyelets 52,54. A receiving body 68 includes a central hollow slot 70 into which a side strap 32 is received. Body further includes a threaded circular bore 72 which is positioned over an eyelet, such as eyelet 52. First, side strap 32 is fed through slot 70 and adjusted to its desired length. Then a set pin, having a head portion shown by knurled ring 74, and a pin portion shown by threaded screw shaft 76, is received through a washer 78 and eyelet 52 and threaded into bore 72 until it bears against side strap 32, thereby holding it in place.

Figure 10:
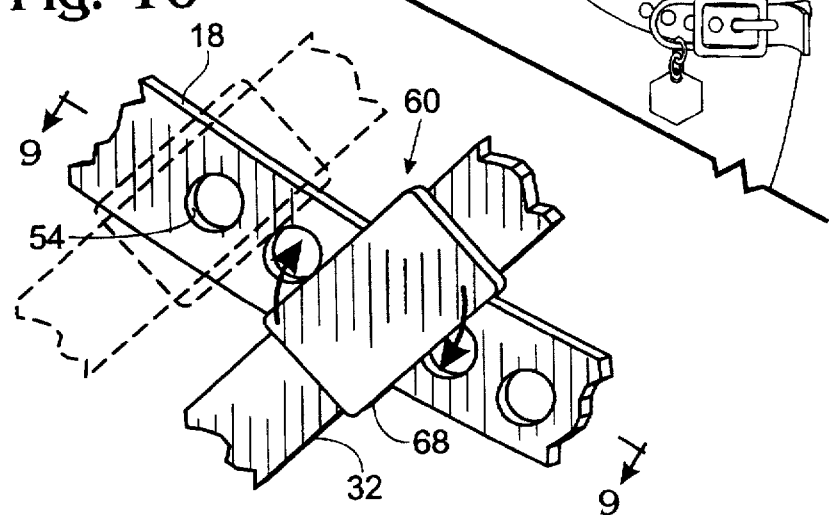
FIG. 10 is a detailed perspective view showing the pivot means feature of the device of FIG. 8.

It will be appreciated that screw shaft 76 has a smaller diameter than eyelet 52 so that the pivot means assembly 60 rotates as shown by the arrows in FIG. 10. It will also be appreciated that the pivot means 60 can be coupled to any one of the plurality of eyelets to laterally adjust the side strap along the length of the collar as illustrated by the dashed lines in FIG. 10.

Having described and illustrated the principles of the invention in a preferred embodiment thereof, it should be apparent that the invention can be modified in arrangement and detail without departing from such principles. For instance, it is understood that the eyelet/snap embodiment shown in FIGS. 6 and 7 can function to pivot the eye enclosure means. Additionally, the eye enclosure means 11 and side straps 30,32 can equivalently be made of a single piece of molded plastic combining the features of the one piece transparent forward element 44 of FIG. 3 with the pivot means of FIGS. 6, 7 or 9. As such, I claim all modifications and variation coming within the spirit and scope of the following claims.

I claim:

1. An eye protection device adapted to be worn by a canine, comprising:
   eye enclosure means having a substantially transparent forward element and a peripheral edge which is adapted to rest snugly against the face of a canine;
   a neck encircling collar adapted to be worn about the neck of the canine;
   anti-loss means for use in cooperation with a conventional dog collar, the anti-loss means comprising an anti-loss strap coupled between the neck encircling collar and the dog collar; and
   left and right side straps coupled on opposing sides of the eye enclosure means and connecting said means to said neck encircling collar.

2. The eye protection device according to claim 1, wherein said left and right side straps include length adjustment means.

3. The device of claim 2, wherein said length adjustment means includes a buckle.

4. The device of claim 2, wherein said length adjustment means includes elongate complementary hook and loop portions mounted on a same side of each of the left and right straps, one portion being adapted to fold over said neck encircling strap and against a second complimentary portion to thereby fasten said straps to said collar.

5. The device of claim 2, wherein said length adjustment means includes a pawl device.

6. The eye protection device according to claim 1, wherein said neck encircling collar includes lateral attachment means adapted to couple said left and right side straps along a selected length of said collar.

7. The device of claim 6, wherein said lateral attachment means includes a plurality snaps disposed along the length of the left and right side straps and a plurality of eyelets disposed along the length of the collar and adapted to receive one of said plurality of snaps.

8. The device of claim 6, wherein said lateral attachment means includes a plurality snaps disposed along the length of the collar and a plurality of eyelets disposed along the length of the left and right side straps and adapted to receive one of said plurality of snaps.

9. The device of claim 1, further including anti-lift means comprising second left and right side straps connected at one end to respective opposing sides of the eye enclosure means and connected at another end to the neck encircling strap in spaced apart relation to said first left and right side straps.

10. The device of claim 1, further including a pair of clear plastic lens units each adapted to enclose an individual eye of the canine and coupled together by lens adjustment means for moving the lens units in relation to one anther, thereby allowing the lens to fit canines having eyes which are various distances apart.

11. An eye protection device adapted to be worn by a canine, comprising:
   eye enclosure means having a substantially transparent forward element;
   a neck encircling collar adapted to be worn about the neck of the canine;
   left and right side straps coupled on opposing sides of the eye enclosure means; and
   pivot means coupled between the left and right side straps and the collar for rotating said forward element from a first lowered position adjacent the eyes of the canine to a second raised position on top of the head of the canine.

12. The device of claim 11 wherein the pivot means includes:
   an eyelet disposed along the length of the collar;
   a receiving body coupled to one of said left and right side straps and having a circular bore defined therein, said body being located on an outer side of said collar and positioned over said eyelet; and
   a set pin including a head portion and a pin portion having a pin axis adapted to extend through said eyelet and be received within said circular bore to thereby allow rotational movement of the receiving body about the pin axis.

13. The device of claim 11 wherein said eye enclosure means and said left and right side straps are integrally formed.

14. The device of claim 11, further including left and right side strap length adjustment and lateral attachment means adapted to couple said left and right side straps along a selected length of said collar.

15. The device according to claim 14, wherein said length adjustment and lateral attachment means and said rotation means includes a plurality of snaps disposed along the length of the left and right side straps and a plurality of eyelets disposed along the length of the collar and adapted to receive one of said plurality of snaps.

16. The device according to claim 14, wherein said length adjustment and lateral attachment means and said rotation means includes a plurality of snaps disposed along the length of the collar and a plurality of eyelets disposed along the length of the left and right side straps and adapted to receive one of said plurality of snaps.

17. The device of claim 14 wherein said length adjustment and lateral attachment means includes an elongate hook and loop portion mounted on the left and right straps and a complementary elongate hook and loop portion mounted along a length of said collar.

18. The device of claim 14, further including anti-lift means comprising second left and right side straps connected at one end to respective opposing sides of the eye enclosure means and connected at another end to the neck encircling strap in spaced apart relation to said first left and right side straps.

19. The device of claim 14, further including anti-loss means for use in cooperating with a conventional dog collar, the anti-loss means comprising an anti-loss strap coupled between the neck encircling collar and the dog collar.

20. The device of claim 14, further including a pair of clear plastic lens units each adapted to enclose an individual eye of the canine and coupled together by lens adjustment means for moving the lens units in relation to one another, thereby allowing the lens to fit canines having eyes which are various distances apart.

* * * * *